(12) United States Patent
You et al.

(10) Patent No.: US 12,140,536 B2
(45) Date of Patent: Nov. 12, 2024

(54) METHOD FOR DETERMINING A GAS CONCENTRATION FROM A GROUP OF SENSORS

(71) Applicant: Senseair AB, Delsbo (SE)

(72) Inventors: Yang You, Solna (SE); Tobias Oechtering, Solna (SE); Henrik Rödjegård, Johanneshov (SE)

(73) Assignee: Senseair AB, Delsbo (SE)

( * ) Notice: Subject to any disclaimer, the term of this patent is extended or adjusted under 35 U.S.C. 154(b) by 0 days.

(21) Appl. No.: 18/022,950

(22) PCT Filed: Aug. 30, 2021

(86) PCT No.: PCT/SE2021/050841
§ 371 (c)(1),
(2) Date: Feb. 23, 2023

(87) PCT Pub. No.: WO2022/050889
PCT Pub. Date: Mar. 10, 2022

(65) Prior Publication Data
US 2023/0236120 A1 Jul. 27, 2023

(30) Foreign Application Priority Data
Sep. 1, 2020 (SE) ................... 2051034-3

(51) Int. Cl.
*G01N 21/3504* (2014.01)
(52) U.S. Cl.
CPC ... *G01N 21/3504* (2013.01); *G01N 2201/127* (2013.01)

(58) Field of Classification Search
CPC ............. G01N 21/3504; G01N 2201/127
See application file for complete search history.

(56) References Cited

U.S. PATENT DOCUMENTS

| | | | |
|---|---|---|---|
| 3,665,748 A | | 5/1972 | Mator |
| 5,429,805 A | * | 7/1995 | Uno ........... G01N 21/3504 250/343 |

(Continued)

FOREIGN PATENT DOCUMENTS

| | | |
|---|---|---|
| CH | 712528 A2 | 12/2017 |
| CN | 1228839 A | 9/1999 |

(Continued)

OTHER PUBLICATIONS

Belief Function Fusion based Self-calibration for Non-dispersive Infrared Gas Sensor, Oct. 25-28, 2020, Yang You, 5 pages (Year: 2020).*

(Continued)

*Primary Examiner* — Tung S Lau
(74) *Attorney, Agent, or Firm* — Knobbe, Martens, Olson, & Bear, LLP

(57) ABSTRACT

A method for determining a measure of a gas concentration from a group of at least two non-dispersive infrared, NDIR, gas sensors (S1-SN) is described. The method comprises the steps of obtaining, at a processing unit (1), from each NDIR gas sensor (S1-SN) a measure of a gas concentration as a belief function Pi(x), which provides a probability as a function of the sensed light intensity at a specific wavelength, merging, in the processing unit, the belief functions Pi(x) to a merged belief function P(x). A computer program performing the method is also described.

12 Claims, 4 Drawing Sheets

Figure 1

(56) References Cited

U.S. PATENT DOCUMENTS

| | | | |
|---|---|---|---|
| 5,728,927 A | 3/1998 | Ong | |
| 5,731,508 A | 3/1998 | Slemeyer | |
| 6,883,651 B2 | 4/2005 | Fukaya | |
| 6,944,566 B2 | 9/2005 | Chen et al. | |
| 7,736,903 B2 | 6/2010 | Lambert et al. | |
| 7,845,206 B2 | 12/2010 | Wohltjen | |
| 7,966,104 B2 | 6/2011 | Srivastava et al. | |
| 9,846,117 B2 | 12/2017 | Zhou et al. | |
| 9,927,356 B2* | 3/2018 | Skibo | G01S 17/88 |
| 10,111,432 B2 | 10/2018 | Peng et al. | |
| 10,113,957 B1* | 10/2018 | Yi | G01N 33/004 |
| 11,747,274 B2 | 9/2023 | Martin | |
| 2003/0109795 A1 | 6/2003 | Weber | |
| 2003/0183765 A1 | 10/2003 | Chen et al. | |
| 2006/0047445 A1 | 3/2006 | Williams et al. | |
| 2006/0144061 A1 | 7/2006 | Badenhorst et al. | |
| 2009/0039267 A1 | 2/2009 | Arndt et al. | |
| 2009/0235720 A1 | 9/2009 | Smith | |
| 2010/0078563 A1* | 4/2010 | Haveri | G01N 21/3504 250/343 |
| 2010/0188232 A1 | 7/2010 | Lambert et al. | |
| 2011/0107813 A1 | 5/2011 | Guth et al. | |
| 2011/0213749 A1 | 9/2011 | Pichon | |
| 2012/0078532 A1* | 3/2012 | Forsyth | G01N 21/274 702/24 |
| 2014/0026149 A1 | 1/2014 | Backensto et al. | |
| 2015/0241359 A1 | 8/2015 | Haveri et al. | |
| 2015/0373285 A1 | 12/2015 | Morris et al. | |
| 2016/0025404 A1 | 1/2016 | Zheng et al. | |
| 2016/0187897 A1 | 6/2016 | Peng et al. | |
| 2017/0254737 A1 | 9/2017 | Ke et al. | |
| 2018/0081330 A1 | 3/2018 | Haslett et al. | |
| 2018/0095028 A1 | 4/2018 | Jourdainne | |
| 2018/0120222 A1 | 5/2018 | Fritz et al. | |
| 2018/0120223 A1 | 5/2018 | Marta et al. | |
| 2018/0156766 A1 | 6/2018 | Zeng et al. | |
| 2018/0252699 A1 | 9/2018 | Dang | |
| 2019/0033274 A1 | 1/2019 | Makaram et al. | |
| 2019/0072489 A1 | 3/2019 | Camargo et al. | |
| 2020/0041158 A1 | 2/2020 | Turney et al. | |
| 2020/0346518 A1 | 11/2020 | Deliwala | |
| 2022/0092241 A1 | 3/2022 | Moradian et al. | |
| 2022/0307975 A1* | 9/2022 | Camargo | G01N 21/314 |
| 2023/0236168 A1 | 7/2023 | Granstam et al. | |
| 2023/0288091 A1 | 9/2023 | Bohlin | |
| 2023/0304924 A1 | 9/2023 | Rödjegård | |
| 2024/0051370 A1 | 2/2024 | Ljungblad et al. | |

FOREIGN PATENT DOCUMENTS

| | | |
|---|---|---|
| CN | 1836154 A | 9/2006 |
| CN | 101027615 A | 8/2007 |
| CN | 101449143 A | 6/2009 |
| CN | 102803936 A | 11/2012 |
| CN | 103175803 A | 6/2013 |
| CN | 103528990 A | 1/2014 |
| CN | 105277502 A | 1/2016 |
| CN | 105319176 A | 2/2016 |
| CN | 105021777 B | 8/2016 |
| CN | 106645587 A | 5/2017 |
| CN | 107271405 A | 10/2017 |
| CN | 107917484 A | 4/2018 |
| CN | 108001221 A | 5/2018 |
| CN | 108279719 A | 7/2018 |
| CN | 108762086 A | 11/2018 |
| CN | 110782640 A | 2/2020 |
| CN | 111855897 A | 10/2020 |
| EP | 2784485 A1 | 10/2014 |
| GB | 2395259 A | 5/2004 |
| GB | 2457660 A | 8/2009 |
| JP | 2010210232 A | 9/2010 |
| JP | 2021006755 A | 1/2021 |
| KR | 10-2016-0122213 A | 9/2016 |
| KR | 101720944 B1 | 4/2017 |
| KR | 10-2019-0074506 A | 6/2019 |
| SE | 531741 C2 | 7/2009 |
| SE | 1950840 | 1/2021 |
| WO | WO 1998/09152 A1 | 3/1998 |
| WO | WO 2006/029920 A1 | 3/2006 |
| WO | WO 2007/091043 A1 | 8/2007 |
| WO | WO 2012/166585 A2 | 12/2012 |
| WO | WO 2016/020422 A1 | 2/2016 |
| WO | WO 2017/162917 A1 | 9/2017 |
| WO | WO 2017/164953 A1 | 9/2017 |
| WO | WO 2018/038491 A1 | 2/2018 |
| WO | WO 2019/115473 A1 | 6/2019 |
| WO | WO 2021/002796 A1 | 1/2021 |

OTHER PUBLICATIONS

International Search Report and Written Opinion in PCT/SE2021/050841 dated Nov. 16, 2021.
A Novel Multi-Criteria Discounting Combination Approach for 1-13, Multi-Sensor Fusion, D Yilin et al, IEEE Sensors Journal, 9411-9421, 2019; abstract.
A new distance based total uncertainty measure in the theory of belief functions, Y Yang and D Han, Knowledge Based Systems 94, 114-123, 2016; whole document.
Novel Algorithm for Identifying and Fusing Conflicting Data in 1-13 Wireless Sensor Networks, A Zhang et al, Sensors, 14, 9562-9581, 2014; whole document.
Combining belief functions based on distance of evidence, D 1-13 Yong et al, Decision support system, 38, 489-493, 2004; whole document.
Sensor fusion Using Dempster-Shafer Theory, H Wu et al, 1-13 IEEE Instrumentation and measurement, Technology Conference, 2002; whole document.
A New Distance Measure of Belief Function in Evidence 1-13 Theory, C Cheng and F Xiao, IEEE Access, 68607-68617, 2019; whole document.
Sensor Fusion Using Dempster-Shafer Theory II: Static 1-13 Weighting and Kalman filter-like Dynamic Weighting, H Wu et al, Instrumentation and measurement, Technology Conference, 2003; whole document.
International Search Report & Written Opinion mailed Jun. 23, 2022 in International Application No. PCT/SE2022/050574.
International Search Report and Written Opinion in PCT/SE2021/050119 dated Apr. 20, 2021 in 13 pages.
International Search Report and Written Opinion in PCT/SE2021/050647 dated Sep. 27, 2021 in 10 pages.
International Search Report and Written Opinion in PCT/SE2021/0510226 dated Jan. 18, 2022 in 10 pages.
International Search Report and Written Opinion in PCT/SE2021/051148 dated Dec. 8, 2021 in 10 pages.
International Search Report and Written Opinion in PCT/SE2021/051308 dated Feb. 17, 2022.
Office Action for Chinese Application No. 202180016930.4 dated Mar. 18, 2023 with translation in 17 pages.
Cited Provisions from Office Action for Chinese Application No. 202180016930.4 dated Mar. 18, 2023 in 1 page.
Hodgkinson et al., "Optical gas sensing: a review", Topical Review, Measurement Science and Technology, vol. 24 No. 1, pp. 1-95, 2013. doi: 10.1088/0957-0233/24/1/012004; figure 15; Section 4.
Ljungblad "High Performance breath alcohol analysis" Malardalen University Press Dissertations No. 240, 2017.
Ruano et al., Prediction of Building's temperature using neural networks models. Energy and Buildings, 2006, vol. 28, No. 6, pp. 682-694.
Vaisala, Vaisala Carbocap® Technology for demanding environments, https://www.vaisala.com/en/vaisala-carbocapr-technology-demanding-environments.
T. Wiezbicki and E. P. Ribeiro, "Sensor drift compensation using weighted neural networks," 2016 IEEE Conference on Evolving and Adaptive Intelligent Systems (EAIS), 2016, pp. 92-97, doi: 10.1109/EAIS.2016.7502497. ; whole document.
Office Action & Search Report dated Dec. 27, 2023 in Chinese Application No. 2021800533305.

(56) References Cited

OTHER PUBLICATIONS

You et al., "Hidden Markov Model Based Data-driven Calibration of Non-dispersive Infrared Gas Sensor," IEEE Xplore page, EUSPICO, pp. 1717-1721, 2020.

* cited by examiner

METHOD FOR DETERMINING A GAS CONCENTRATION FROM A GROUP OF SENSORS

TECHNICAL FIELD

The present invention relates to determination of a gas concentration from a group of at least two non-dispersive infrared, NDIR, gas sensors.

BACKGROUND ART

Gas sensors are devices used to measure the presence or concentration of gases in an area and play an important role in many applications. A non-dispersive infrared sensor (NDIR sensor) is simple spectroscopic sensor in which a nondispersive element is used to filter out the broad-band light into a narrow spectrum suitable to sense a specific gas. However, NDIR sensors have been recognized to be sensitive to variations of ambient temperature, atmospheric pressure, humidity and some other environmental factors. Moreover, aging of the sensor components also results in inaccuracy of the sensors. Due to this, regular calibration is needed for long-term accuracy of the sensors.

Today, state of the art of infrared gas sensor self-calibration is the well-established ABC technology (Automatic Baseline Correction) where the sensor is calibrated to a fixed value that is assumed to be the fresh air gas concentration. However, this method does not work well in mega-cities where the sensors never get exposed to fresh air. Thus, designing more robust and smart self-calibration algorithms which can be widely applied in different environments becomes more and more important.

SUMMARY OF THE INVENTION

An object of the present invention is to provide a method for determination of a gas concentration from a group of at least two non-dispersive infrared, NDIR, gas sensors, which provides a more reliable result than the methods according to the prior art.

Another object of the present invention is to provide a method for determination of a gas concentration from a group of at least two non-dispersive infrared, NDIR, gas sensors, which takes care of aging of NDIR gas sensors in a better way than the methods according to the prior art.

Another object of the present invention is to provide a computer program for determination of a gas concentration from a group of at least two non-dispersive infrared, NDIR, gas sensors which provides a more reliable result than the methods according to the prior art.

At least one of these objects is fulfilled with a method and a computer program according to the independent claims.

Further advantages are achieved with the features of the dependent claims.

According to a first aspect of the invention a method is provided for determining a measure of a gas concentration from a group of at least two non-dispersive infrared, NDIR, gas sensors, wherein the method comprises the steps of obtaining, at a processing unit, from each NDIR gas sensor a measure of a gas concentration as a belief function, which is a probability as a function of the measure of the gas concentration at a specific wavelength, and merging, in the processing unit, the belief functions $P_i(x)$ to a merged belief function $P(x)$.

The measure of the gas concentration may be an intensity value of the light that penetrates the gas. The gas sensor may also be configured to transform the intensity value to a gas concentration. In this case the measure of the gas concentration is the gas concentration. If the transformation from the light intensity to the gas concentration is known to the processing unit performing the method it is possible to use the light intensity. If, however, the transformation from the light intensity to the gas concentration is not known to the processing unit the belief functions are preferably a probability as a function of the gas concentration. The gas sensors measure a light intensity and include the self-awareness on the uncertainty of the sensor in the measurement. The measurement may then be sent from the gas sensor as the probability as a function of the light intensity. Alternatively the light intensities may be transformed into gas concentrations and the belief function may be sent from the gas sensor as the gas concentration as a function of the gas concentration.

By using NDIR sensors which provide a gas concentration measurement as a belief function, which provides a probability as a function of the sensed gas concentration at a specific wavelength, i.e., measured at a specific wavelength, it is possible to reduce the uncertainty on the actual gas concentration, which results in a better gas measurement at this present moment.

NDIR sensors which provides belief functions may be configured in many different ways. One alternative for such an NDIR sensor is to use oversampling, i.e., the sensor outputs sensor readings at a lower frequency than a frequency at which it obtain measures of the gas concentration. The variation in the measure may be provided as the belief function.

Alternatively the NDIR sensor which provides a belief function may be configured to obtain a measure of the gas concentration and to output the measure as a Gaussian distribution around the obtained measure of the gas concentration.

Alternatively the NDIR sensor may be configured to use a model which includes the knowledge on the physics of the NDIR gas sensor. Using the Lambert-beer law as basis of the model, we can learn the statistical behaviour of the sensor using supervised or unsupervised machine learning algorithms. In particular, such a model can compensate for environmental factors such as temperature.

The method may also comprise the step of calibrating each NDIR gas sensor using the merged belief function $P(x)$. By calibrating each NDIR gas sensor with the merged belief function $P(x)$ the self-awareness of each NDIR sensor will be improved and further measurements with the NDIR gas sensor will be more accurate.

The processing unit may be a central processing unit which is in communication with each one of the NDIR gas sensors. By having a central processing unit the measurement of the measure of the gas concentration may be performed with different NDIR gas sensors in different measurements, wherein the selection of NDIR sensors is done by the central processing unit.

The merging of the belief functions $P_i(x)$ may be performed using the Dempster-Shafer theory. The Dempster-Shafer theory is well known per se, but has not been used for the present purpose.

The merging of the belief functions $P_i(x)$ may comprise calculation of a weighted average $P(x)$ of the belief functions $P_i(x)$, wherein the weight of each belief function is dependent on the distance $W(P_i(x), P_j(x))$ between each belief function $P_i(x)$ and the other belief functions $P_{j,\, j\neq i}(x)$ such that an increased distance $W_2(P_i(x), P_j(x))$ of a belief function $P_i(x)$ from the other belief functions $P_{j, j\neq i}(x)$ results in a decreased weight of the belief function $P_i(x)$.

The calculation of a weighted average $P(x)$ of the belief functions $P_i(x)$ constitutes an extension of the Dempster-Shafer method. The weighting of the average takes care of the problem when the belief functions are conflicting. By weighting the average in this way the belief functions of NDIR gas sensors which differ much from a majority of belief functions, which are close to each other, will not affect the merged belief function as much as the majority of belief functions, which are close to each other.

The distance between two belief functions $P_i(x)$, $P_j(x)$ used in the weighting of the belief functions $P_i(x)$ is determined as the Wasserstein distance $W_p$, where $W_p$, p>1 for two probability measures $P_i$ and $P_j$ defined on the gas concentration range is given by $$W_p(P_i, P_j) = \left( \inf_{(\hat{P}_i, \hat{P}_j) \in \Gamma(P_i, P_j)} \mathbb{E}\{d(\hat{P}_i, \hat{P}_j)^p\} \right)^{1/p}$$

wherein I(Pi, Pj) denotes the set of joint probability measures $P_{ij}$ defined on the gas concentration range, with marginals $P_i$ and $P_j$ and d denotes the distance of the gas concentration values from the corresponding random variables of the gas concentration range. It is favourable to use the Wasserstein distance in the calculations as this discriminates belief functions which differ from the majority of belief functions which measures well the similarity.

The support degree of a given belief function may be calculated as $$Supp(P_i(x)) = \sum_{j=1, j\neq i}^{N} S(P_i(x), P_j(x))$$

wherein $$S(P_i(x), P_j(x)) = 1 - \hat{W}_2(P_i(x), P_j(x))$$

and wherein $$\hat{W}_2(P_i(x), P_j(x)) = \frac{2 \times W_2(P_i(x), P_j(x))}{\sum_i \sum_j W_2(P_i(x), P_j(x))}.$$

The corresponding weighting factor of belief function $P_i$ is then obtained after normalization, where the weighting factor $a_i$ is expressed as $$\frac{Supp(P_i(x))}{\sum_{i=1}^{N} Supp(P_i(x))}.$$

The weighted average of all the N belief functions can be expressed $$\hat{P}(x) = \sum_{i=1}^{N} \alpha_i P_i(x)$$

which is used to compute the final belief function for each sensor. There are alternative ways to use the weighted average to compute the merged belief, for instance it is possible to use the Dempster-Shafer rule applied to the weighted average belief function with itself N-1 times.

The method may also comprise the step of selecting the NDIR gas sensors in the group from a plurality of NDIR gas sensors, wherein each NDIR gas sensor of the plurality of NDIR gas sensors is related to a present position, and wherein the NDIR gas sensors are selected based on their present position. The NDIR gas sensors preferably have a positioning sensor such as, e.g., a GPS sensor to determine its position. By selecting the NDIR gas sensors in the group from a plurality of NDIR gas sensors it is possible to select gas sensors which are close to a position where a measurement is to be made. The NDIR gas sensors may for example be positioned in cars which move around.

The NDIR gas sensors may also be related to historic positions and wherein the NDIR gas sensors are also selected based on their historic positions. By having the NDIR gas sensors related also to historic positions it is possible to select such gas sensors that have recently been in an environment with a known gas concentration or has recently been calibrated.

That the NDIR gas sensors are related to historic positions may be implemented by storing in the processing unit information on positions together with corresponding points in time.

For a car having a gas sensor measuring the $CO_2$ concentration an environment with a known gas concentration may, in the case of $CO_2$, be on the countryside. The sensors are more reliable if they have self-calibrated on the countryside. With regard to recent calibration the NDIR gas sensors may store information on when it was last calibrated.

The NDIR gas sensors may also be selected based on the gas concentration measurements of the NDIR gas sensors. If one gas sensor provides very different gas concentrations compared with the rest of the gas sensors the gas sensor providing very different gas concentrations may be de-selected before the next measurement. In this way the quality of the measurements may be improved.

The selection of NDIR gas sensors may be performed repeatedly over time. If the object of a measurement is to measure the concentration of a gas at a specific position, the gas sensors selected for each measurement are the gas sensor being close to the specific position.

According to a second aspect of the present invention a computer program is provided for determining a gas concentration from a group of at least two non-dispersive infrared gas, NDIR, sensors, comprising instructions which, when executed by a processor in a processing unit causes the processor unit to control the processing unit to carry out the method according to the first aspect of the invention or any of the embodiments described above.

According to a third aspect of the present invention as processing unit is provided, which is configured for determining a gas concentration from a group of at least two non-dispersive infrared gas, NDIR, sensors, wherein the processing unit is configured to obtain from each NDIR gas sensor a measure of a gas concentration as a belief function, which is a probability as a function of the measure of the gas concentration at a specific wavelength, i.e., measured at a specific wavelength, merging, in the processing unit, the belief functions $P_i(x)$ to a merged belief function $P(x)$.

DETAILED DESCRIPTION

Figure 1:
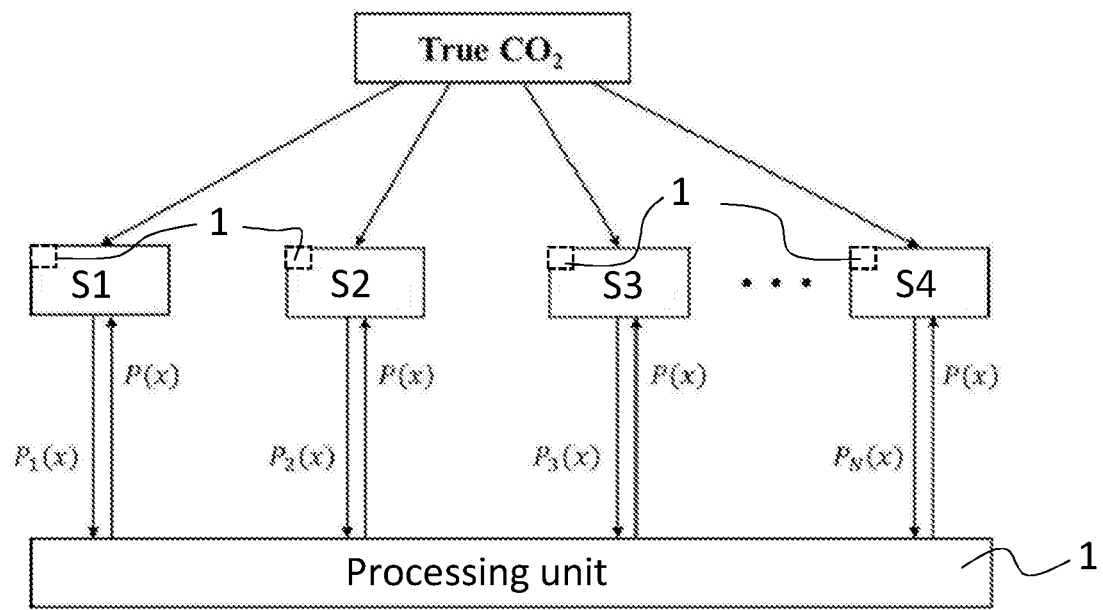
FIG. 1 shows system with a group of gas sensors which are in communication with a processing unit which is configured to perform the method according to the present invention.

In the following detailed description of the invention similar features in the different figures will be denoted with the same reference numeral.

FIG. 1 shows a system with a group of N gas sensors S1-SN which are in communication with a processing unit which is configured to perform the method according to the present invention. All gas sensors preferably communicate wirelessly with the processing unit. According to an alternative embodiment the processing unit 1 may be integrated in at least one of the gas sensors. According to another alternative a processing unit 1 may be integrated in all of the gas sensors S1-SN. According to this alternative embodiment all gas sensors communicate with each other and each processing unit performs the method according to an embodiment of the invention.

According to the embodiment with a separate processing unit 1, the processing unit obtains from each NDIR gas sensor a measure of a gas concentration as a belief function, which provides a probability as a function of the sensed light intensity measured at a specific wavelength, providing the belief functions from each one of the NDIR gas sensors to a processing unit, and merging, in the processing unit 1, the belief functions $P_i(x)$ to a merged belief function $P(x)$. The merged belief function $P(x)$ provides a more reliable measure of the gas concentration. In order to further improve future measurements of the gas concentration the processing unit 1 may provide the merged belief function to each one of the gas sensors S1-SN for calibration of the gas sensors S1-SN.

Figure 2:
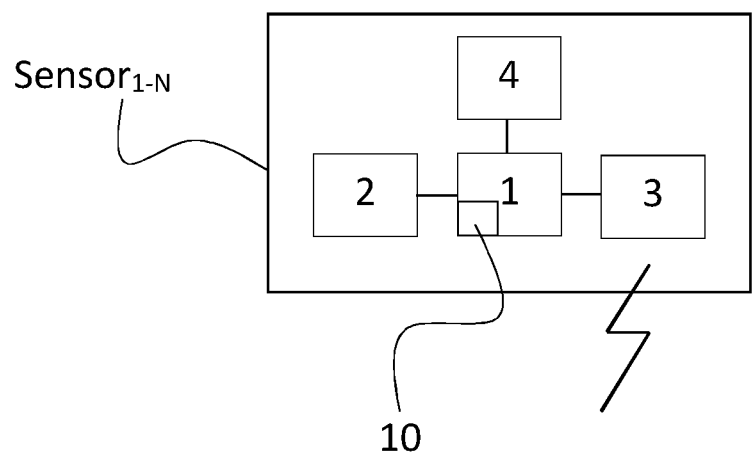
FIG. 2 shows different belief functions provided from the gas sensors in the system of FIG. 1.

FIG. 2 shows schematically a gas sensor S1-SN according to an embodiment of the present invention. The gas sensor S1-SN comprises an NDIR sensing unit 2, a processing unit 1 and a communication interface 3. The processing unit 1 obtains a measure of the gas concentration from the NDIR sensing unit 2 and controls the sending of the measure of the gas concentration from the gas sensor S1-SN to the other gas sensors S1-SN. The gas sensor S1-SN also comprises a positioning sensor 4 such as a, e.g., GPS sensor, which enables the gas sensor S1-SN to determine its position.

Figure 3:
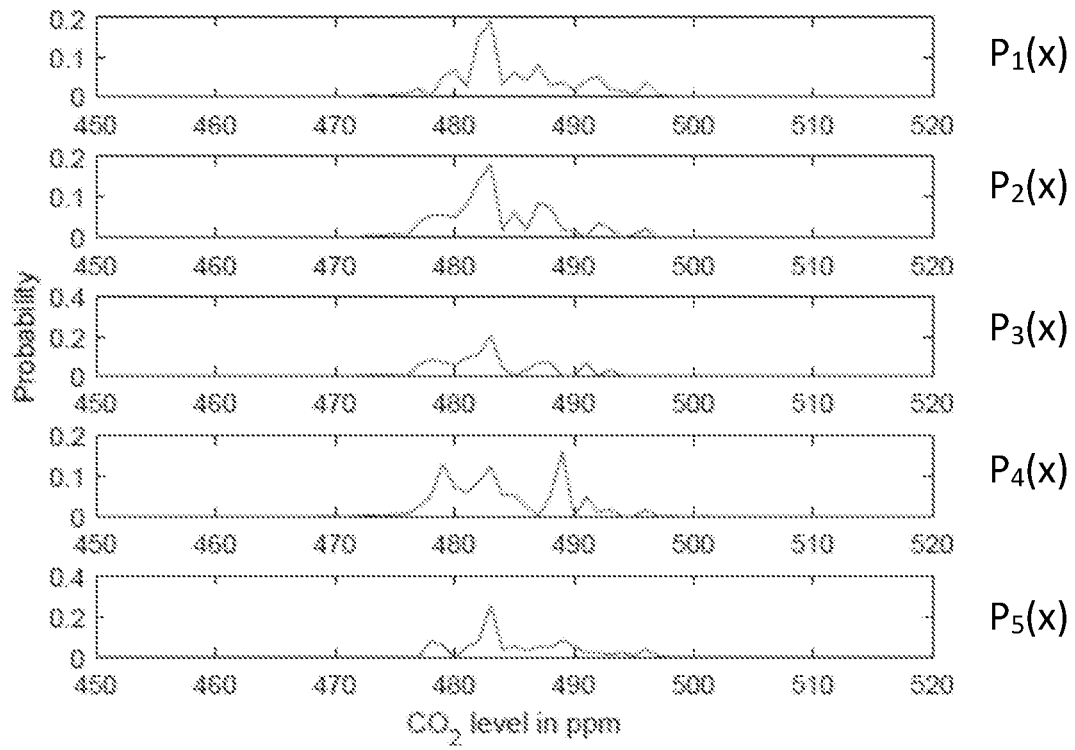
FIG. 3 shows five different belief functions $P_1(x)$-$P_5(x)$ provided from the gas sensors S1-SN in the system of FIG. 1.

FIG. 3 shows five different belief functions $P_1(x)$-$P_5(x)$ provided from the gas sensors S1-SN in the system of FIG. 1. Each belief function $P_1(x)$-$P_5(x)$ shows the probability as a function of $CO_2$ concentration. As can be seen in FIG. 3 the belief functions $P_1(x)$-$P_5(x)$ extend over a large concentration span.

Figure 4:
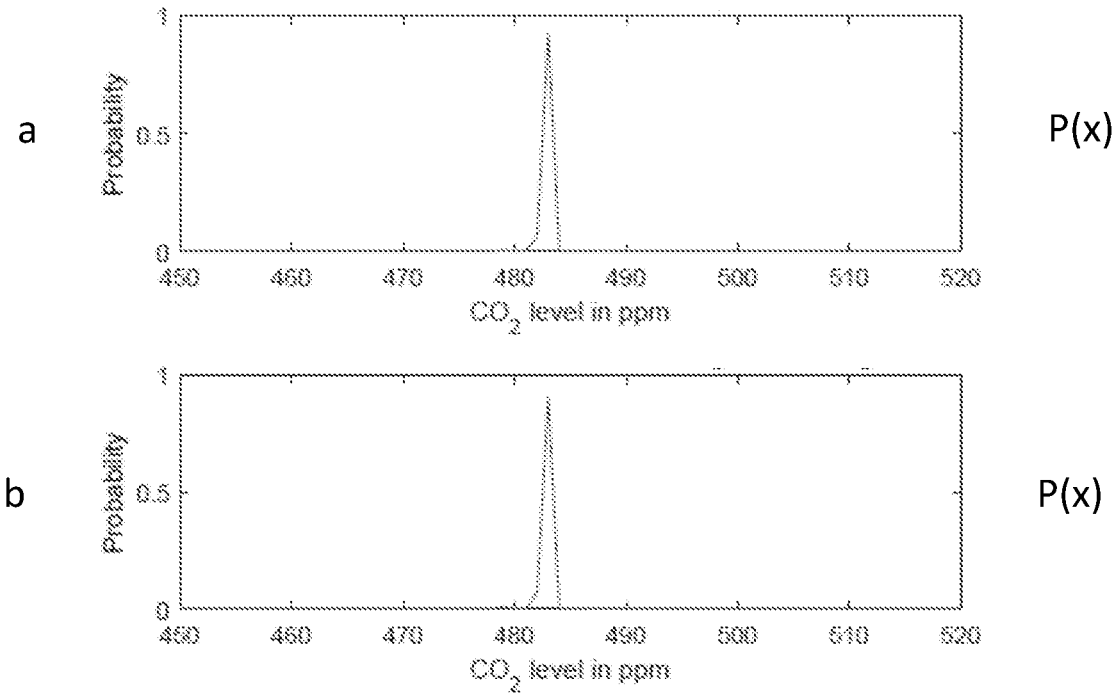
FIGS. 4a and 4b show the merged belief function resulting from merging the belief functions in FIG. 3 using Dempster-Shafer rules for merging and weighted averages, respectively.

FIGS. 4a and 4b shows the merged belief function resulting from merging the belief functions in FIG. 3 using Dempster-Shafer rules for merging and weighted averages, respectively. Both different merging techniques result in similar resulting merged belief function $P(x)$. Both merging techniques result in a probability peak at 482 ppm of $CO_2$.

Figure 5:
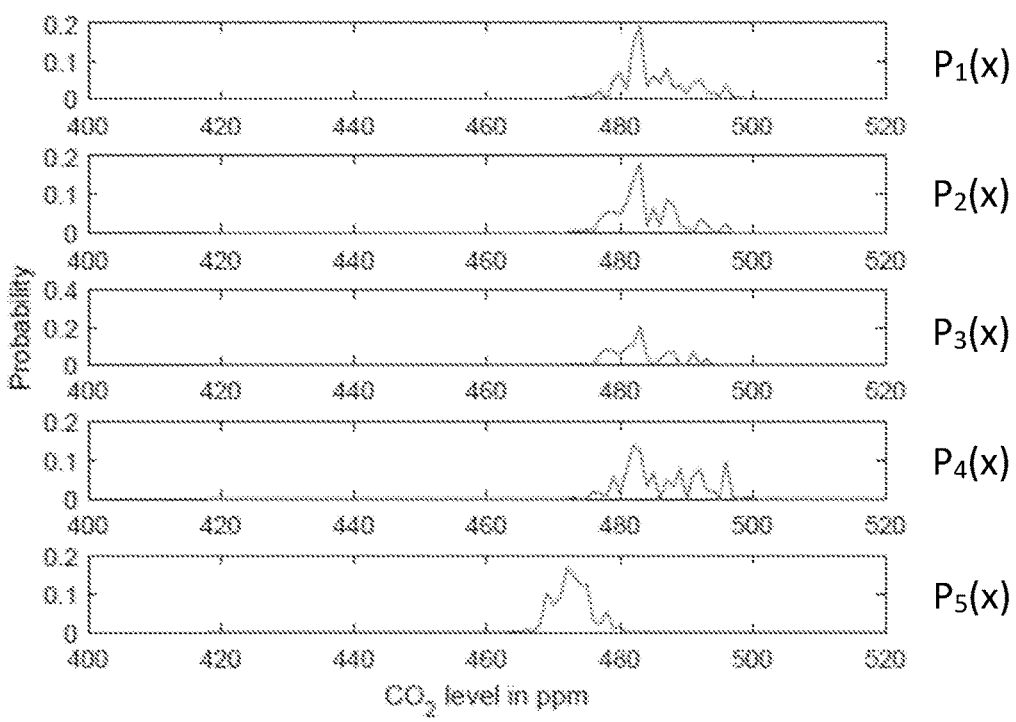
FIG. 5 shows another example of different belief functions $P_1(x)$-$P_5(x)$ provided from the gas sensors in the system of FIG. 1.

FIG. 5 shows another example of different belief functions $P_1(x)$-$P_5(x)$ provided from the gas sensors in the system of FIG. 1. Each belief function $P_1(x)$-$P_5(x)$ shows the probability as a function of $CO_2$ concentration. As can be seen in FIG. 3 the belief functions $P_1(x)$-$P_5(x)$ extend over a large concentration span. As can be seen in FIG. 5 the fifth belief function $P_5(x)$ is visibly shifted to lower $CO_2$ concentrations than the other belief functions $P_1(x)$-$P_4(x)$.

Figure 6:
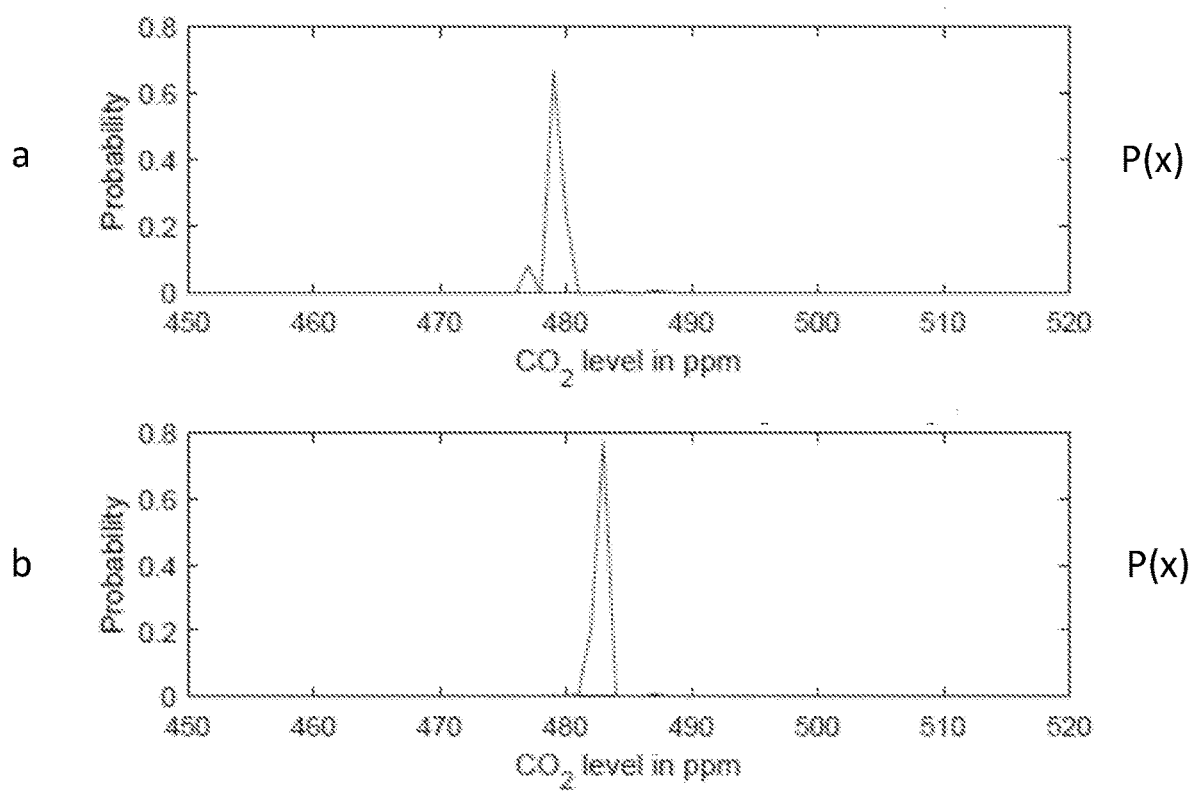
FIG. 6 shows schematically a gas sensor according to an embodiment of the present invention.

FIGS. 6a and 6b shows the merged belief function resulting from merging the belief functions in FIG. 5 using the Dempster-Shafer rules for merging and weighted averages, respectively. As can be seen in FIG. 6 the merging of the belief functions $P_1(x)$-$P_5(x)$ using the Dempster-Shafer rules results in a merged belief function $P(x)$ with a clear probability peak at 479 ppm in $CO_2$ concentration. The merging of the of the belief functions $P_1(x)$-$P_5(x)$ using weighted averages results in a merged belief function $P(x)$ with a clear probability peak at 482 ppm in $CO_2$ concentration. Thus, when merging using weighted averages the effect of the fifth belief function $P_5(x)$ is diminished. It is probable that the fifth gas sensor has drifted and provides an erroneous result. Thus, it is favourable to diminish the effect of the fifth gas sensor Sensors.

In the following it will be described in more detail how a merged belief function $P(x)$ may be achieved and calculated.

The distance between two belief functions $P_i(x)$, $P_j(x)$ used in the weighting of the belief functions $P_i(x)$ is determined as the Wasserstein distance $W_p$, where $W_p$, $p \geq 1$ for two probability measures $P_i$ and $P_j$ defined on the gas concentration range is given by $$W_p(P_i, P_j) = \left( \inf_{(\hat{P}_i, \hat{P}_j) \in \Gamma(P_i, P_j)} \mathbb{E}\{d(\hat{P}_i, \hat{P}_j)^p\} \right)^{1/p}$$

wherein $I(P_i, P_j)$ denotes the set of joint probability measures $P_{ij}$ defined on the gas concentration range, with marginals $P_i$ and $P_j$ and d denotes the distance of the gas concentration values from the corresponding random variables. It is favourable to use the Wasserstein distance in the calculations as this discriminates belief functions which differ from the majority of belief functions which measures well the similarity.

The support degree of a given belief function may be calculated as $$Supp(P_i(x)) = \sum_{j=1, j \neq i}^{N} S(P_i(x), P_j(x))$$

wherein $$S(P_i(x), P_j(x)) = 1 - W_2(P_i(x), P_j(x))$$

and wherein $$\hat{W}_2(P_i(x), P_j(x)) = \frac{2 \times W_2(P_i(x), P_j(x))}{\sum_i \sum_j W_2(P_i(x), P_j(x))}.$$

The corresponding weighting factor of belief function Pi is then obtained after normalization, where the weighting factor $a_i$ is expressed as $$\frac{Supp(P_i(x))}{\sum_{i=1}^{N} Supp(P_i(x))}.$$

The weighted average of all the N belief functions can be expressed $$\hat{P}(x) = \sum_{i=1}^{N} \alpha_i P_i(x)$$

which is used to compute the final belief function for each sensor. There are alternative ways to use the weighted average to compute the merged belief, for instance it is possible to use the Dempster-Shafer rule applied to the weighted average belief function with itself N-1 times.

Figure 7:
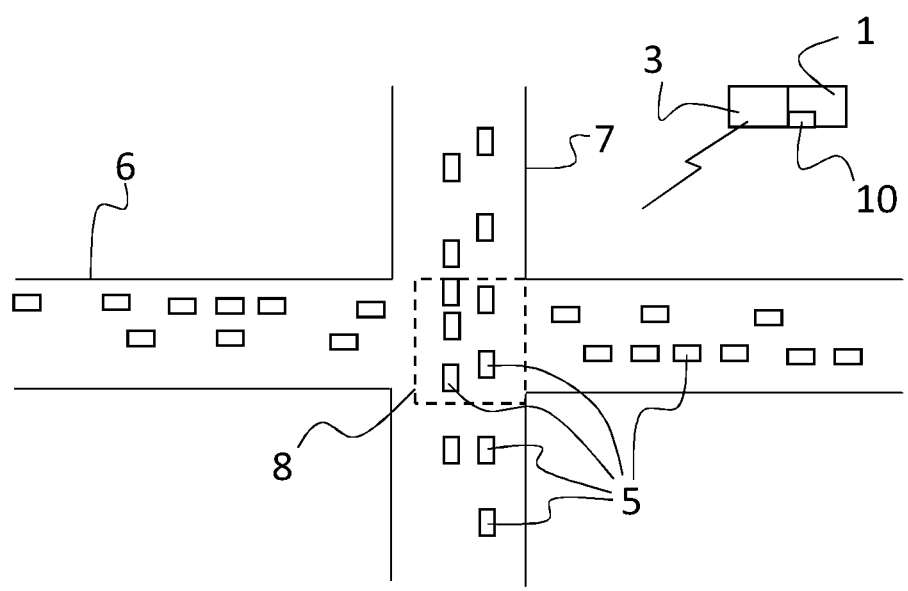
FIG. 7 shows a plurality of cars which each comprises a gas sensor.

FIG. 7 shows a plurality of vehicles 5, which each comprises a gas sensor S1-SN (FIG. 2), at an intersection between two streets 6, 7. In the embodiment shown in FIG. 7 a processing unit 1, comprising a processor 10, is arranged at a fixed position which may be remote to the intersection. The processing unit 1 is connected to a communication interface 3 which communicate with the communication interfaces of the gas sensors S1-SN in the vehicles 5. The processing unit 1 selects the vehicles 5 which are positioned in the middle of the intersection within the dashed rectangle 8. The positions are determined using the positioning sensor 4 in each gas sensor S1-SN. After having received the belief functions $P_i(x)$ from each gas sensor S1-SN the processing unit 1 may calculate a merged belief function P(x) as has been described above.

The above described embodiments may be amended in many ways without departing from the scope of the invention which is limited only by the appended claims.

The invention claimed is:

1. A method for determining a measure of a gas concentration at a measurement position, from a group of at least two non-dispersive infrared, NDIR, gas sensors (S1-SN), wherein the method comprises:
   obtaining from each one of a plurality of NDIR gas sensors (S1-SN) information on their respective present position,
   selecting, from the plurality of NDIR gas sensors, a group of at least two NDIR gas sensors (S1-SN) having a present position close to the measurement position,
   obtaining, at a processing unit, from each selected NDIR gas sensor (S1-SN) a measure of a gas concentration as a belief function $P_i(x)$, which is a probability as a function of the measure of the gas concentration at a specific wavelength, and
   merging, in the processing unit, the belief functions $P_i(x)$ to the measure of the gas concentration as a merged belief function P(x).

2. The method according to claim 1, also comprising the step of calibrating each NDIR gas sensor using the merged belief function P(x).

3. The method according to claim 1, wherein the processing unit is a central processing unit (1) which is in communication with each one of the NDIR gas sensors (S1-SN).

4. The method according to claim 1, wherein the merging of the belief functions Pi(x) is performed using the Dempster-Shafer rules for merging.

5. The method according to claim 1, wherein the merging of the belief functions Pi(x) comprises calculation of a weighted average P(x) of the belief functions $P_i(x)$, wherein the weight of each belief function is dependent on the distance $W(P_i(x), P_j(x))$ between each belief function $P_i(x)$ and the other belief functions $P_{j, j \neq i}(x)$ such that an increased distance $W_2(P_i(x), P_j(x))$ of a belief function $P_i(x)$ from the other belief functions $P_{j, j \neq i}(x)$ results in a decreased weight of the belief function $P_i(x)$.

6. The method according to claim 5 wherein the distance between two belief functions $P_i(x)$, $P_j(x)$ used in the weighting of the belief functions $P_i(x)$ is determined as the Wasserstein distance $W_p$, where $W_p$, $p \geq 1$ for two probability measures $P_i$ and $P_j$ defined on the gas concentration range is given by $$W_p(P_i, P_j) = \left( \inf_{(\hat{P}_i, \hat{P}_j) \in \Gamma(P_i, P_j)} \mathbb{E}\{d(\hat{P}_i, \hat{P}_j)^p\} \right)^{1/p}$$

wherein $\tau(Pi, Pj)$ denotes the set of joint probability measures $P_{ij}$ defined on the gas concentration range, with marginals $\hat{P}_i$ and $P_j$ and d denotes the distance of the gas concentration values from the corresponding random variables.

7. The method according to claim 6, wherein the support degree $Supp(P_i(x))$ of a given belief function $P_i(x)$ is calculated as $$Supp(P_i(x)) = \sum_{j=1, j \neq i}^{N} S(P_i(x), P_j(x))$$

wherein $$S(P_i(x), P_j(x)) = 1 - \hat{W}_2(P_i(x), P_j(x))$$

wherein $$\hat{W}_2(P_i(x), P_j(x)) = \frac{2 \times W_2(P_i(x), P_j(x))}{\sum_i \sum_j W_2(P_i(x), P_j(x))}$$

wherein the weighting factor $a_i$ is expressed as $$\frac{Supp(P_i(x))}{\sum_{i=1}^{N} Supp(P_i(x))}$$

and wherein the weighting factor $a_i$ is used in the merging of the belief functions $P_i(x)$.

8. The method according to claim 1, wherein the method further comprises selecting the NDIR gas sensors (S1-SN) in the group from a plurality of NDIR gas sensors, wherein each NDIR gas sensor (S1-SN) of the plurality of NDIR gas sensors is related to a present position, and wherein the NDIR gas sensors (S1-SN) are selected based on their present position.

9. The method according to claim 8, wherein the NDIR gas sensors (S1-SN) are further related to historic positions and wherein the NDIR gas sensors (S1-SN) are selected based on their historic positions.

10. The method according to claim 8, wherein the NDIR gas sensors are also selected based on the gas concentration measurements of the NDIR gas sensors (S1-SN).

11. The method according to 8, wherein the selection of NDIR gas sensors (S1-SN) is performed repeatedly over time.

12. A non-transitory computer program readable medium comprising instructions for determining a gas concentration from a group of at least two non-dispersive infrared, NDIR, gas sensors (S1-SN), said instructions which, when executed by a processor in a processing unit causes the processing unit to control the processing unit to carry out the method according to claim 1.

\* \* \* \* \*